US006737405B2

(12) United States Patent
Roemisch et al.

(10) Patent No.: US 6,737,405 B2
(45) Date of Patent: May 18, 2004

(54) STABILIZED PROTEIN PREPARATION AND PROCESS FOR ITS PREPARATION

(75) Inventors: Juergen Roemisch, Marburg (DE); Harald Stauss, Dautphetal (DE); Hans-Arnold Stoehr, Wetter (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/849,343

(22) Filed: May 7, 2001

(65) Prior Publication Data

US 2001/0051154 A1 Dec. 13, 2001

(30) Foreign Application Priority Data

May 8, 2000 (DE) .......................................... 100 22 092

(51) Int. Cl.$^7$ ........................ A61K 38/00; A61K 35/16; C07K 17/10; C07K 16/00
(52) U.S. Cl. ............................. 514/12; 514/23; 514/53; 530/350; 530/383; 530/384; 530/387.1; 530/390.1; 530/390.5; 530/414
(58) Field of Search .............................. 514/12, 53, 23; 530/383, 384, 350, 387.1, 390.1, 390.5, 414

(56) References Cited

U.S. PATENT DOCUMENTS

| | | | |
|---|---|---|---|
| 4,297,344 A | 10/1981 | Schwinn et al. | |
| 4,440,679 A | 4/1984 | Fernandes et al. | |
| 4,623,717 A | 11/1986 | Fernandes et al. | |
| 4,806,524 A | 2/1989 | Kawaguchi et al. | |
| 4,960,757 A | 10/1990 | Kumpe et al. | |
| 5,043,428 A | * 8/1991 | Heimburger et al. | |
| 5,068,106 A | 11/1991 | Paques et al. | |
| 5,248,767 A | 9/1993 | Müller et al. | |
| 6,239,261 B1 | 5/2001 | Heimburger et al. | |
| 6,514,940 B2 | * 2/2003 | Romisch et al. | |

FOREIGN PATENT DOCUMENTS

| | | |
|---|---|---|
| CA | 2251262 | 5/1999 |
| DE | 29 16 711 | 11/1980 |
| EP | 1 008 350 A1 | 6/2000 |
| GB | 0077355 B1 * | 4/1983 |

* cited by examiner

Primary Examiner—Christina Chan
Assistant Examiner—Phuong Huynh
(74) Attorney, Agent, or Firm—Finnegan, Henderson, Farabow, Garrett and Dunner, L.L.P.

(57) ABSTRACT

A stabilized protein preparation is described which contains no antithrombin III and is protected against loss of activity during pasteurization by the addition of stabilizers which comprise one or more saccharides as a mixture with more than 0.5 mol/l of one or more amino acids chosen from the group arginine, lysine, histidine, phenylalanine, tryptophan, tyrosine, aspartic acid and its salts or glutamic acid and its salts. Glycine and/or glutamine can also be additionally added to each of these amino acids. A process for the viral inactivation or viral depletion of a protein preparation of this type which contains the abovementioned stabilizers and is subjected to pasteurization or viral depletion by filtration, centrifugation or treatment with detergents or bactericidal or virucidal agents is also described.

11 Claims, No Drawings

STABILIZED PROTEIN PREPARATION AND PROCESS FOR ITS PREPARATION

The invention relates to a stabilized protein preparation which contains therapeutically active proteins and is protected against a loss of action or the denaturation of the proteins during pasteurization by the addition of stabilizers. Moreover, processes for viral inactivation and viral depletion of the protein preparations stabilized according to the invention are described. These include, inter alia, nanofiltration and treatment with bactericidal or virucidal substances or detergents.

It is known that certain proteins are employed in the form of concentrates for the prophylaxis and therapy of different diseases which are caused by hereditary or acquired deficiency states of these proteins. Blood plasma or organ extracts particularly serve here as a source of the therapeutically administered proteins. Recently, appropriate proteins prepared recombinantly or transgenically have also been therapeutically administered.

Each of the sources mentioned involves, however, the potential risk of an introduction of infectious organisms such as bacteria, viruses and prions. Therefore, numerous processes have also already been developed which can counteract such a potential contamination of protein preparations. With pasteurization, in particular the heating of protein solutions at 60° C. for a period of 10 hours, a very effective process for the inactivation of infectious viruses and other pathogens is already available which has decisively improved the safety standard with respect to the transmission of infections by protein preparations. In addition, further procedures have been developed such as the treatment of the preparations with detergents or bactericidal or virucidal agents. Moreover, mechanical separation of organisms, for example, by means of a suitable filtration such as "nanofiltration", can also be carried out.

However, it is not sufficient to make procedures available which ensure reliable inactivation or depletion of viruses and other pathogenic microorganisms in protein preparations. At the same time, care must also be taken that the therapeutic efficacy of the protein preparation is not adversely affected by measures for viral inactivation or viral depletion. Therefore, the changes to be attributed most to conformational changes of the proteins must be counteracted by the addition of stabilizers to the protein solution to be heated. Although stabilizers are already generally used as additives to protein preparations, their qualitative and quantitative composition must be suited to certain proteins or protein groups of similar physicochemical properties. In this case carbohydrates are often used, not infrequently in combination with certain amino acids.

Thus, DE-A-29 16 711 describes a process for the stabilization of blood clotting factors in which an amino acid and a mono- or oligosaccharide or a sugar alcohol are added to the protein solution. The amino acids employed therein are glycine, $\alpha$- or $\beta$-alanine, hydroxyproline, proline, glutamine and $\alpha$-, $\beta$- or $\gamma$-aminobutyric acid.

U.S. Pat. Nos. 4,440,679 and 4,623,717 disclose that heat-sensitive, therapeutically active proteins such as factor VIII, fibronectin, antithrombin III, $\alpha$-antitrypsin, plasminogen, albumin and prekallikrein can be pasteurized without loss of activity if either a concentrated aqueous solution of a sugar or of a reduced sugar which also can additionally contain 0.1 to 0.5 mol/l of an amino acid, in particular arginine, lysine and/or glycine, is added to them.

Finally, German patent application 198 564 43.0 also describes a stabilized antithrombin III preparation which is protected against loss of activity during pasteurization by the addition of stabilizers which contain one or more saccharides as a mixture with more than 0.5 mol/l of one or more amino acids chosen from the group arginine, lysine, histidine, phenylalanine, tryptophan, tyrosine, aspartic acid and its salts or glutamic acid and its salts, where glycine and/or glutamine can also be additionally added to each of these amino acids.

It has now been found that other therapeutically valuable proteins which contain no antithrombin III can be stabilized according to the process described in German patent application 198 564 43.0 such that they survive pasteurization or another procedure for viral inactivation or viral depletion almost intact. The proteins to be stabilized by this procedure can be prepared either from plasma or organ extracts. In particular, blood clotting factors II, V, VII and VIIa (activated form of FVII), VIII, IX, X, XII and XIII, and their combination preparations such as the "prothrombin complex concentrate" consisting of FII, FVII, FIX and FX, and the activated prothrombin complex concentrate and also FIIa (thrombin) can thus be stabilized with very good success. The same effect was also observed in the case of von Willebrand factor (vWF) or FVIII/vWF, in the case of albumins, in the case of immunoglobulins, protease inhibitors, such as the C1 inhibitor, $\alpha$-2-antiplasmin and $\alpha$-1-antitrypsin, protein C and activated protein C, protein S, protein Z, the inhibitor of clotting initiated by tissue thromboplastin (TFPI=tissue factor pathway inhibitor), as well as fibrinogen, fibronectin and plasminogen.

Protein preparations stabilized according to the invention also can be prepared either from appropriate recombinant or transgenic proteins.

The invention therefore relates to a stabilized protein preparation which contains no antithrombin III and is protected against a loss of activity during pasteurization by the addition of stabilizers which comprise one or more saccharides as a mixture with more than 0.5 mol/l of one or more amino acids chosen from the group arginine, lysine, histidine, phenylalanine, tryptophan, tyro sine, aspartic acid and its salts or glutamic acid and its salts, where glycine and/or glutamine can also be additionally added to each of these amino acids.

As saccharide, the protein preparation stabilized according to the invention contains a monosaccharide, a disaccharide or an oligosaccharide in an amount of at least 0.5 g/ml, preferably of at least 1.0 g/ml, and more preferably of at least 1.5 g/ml. The preparation has a pH of 3.0 to 9.5, preferably of 4.0 to 8.5. It moreover contains one or more of the abovementioned amino acids in a concentration of more than 0.5 mol/l, preferably of more than 0.8 mol/l.

Mixtures of a saccharide in a concentration of more than 1.5 g/ml with one or more of the abovementioned amino acids in concentrations of over 0.5 mol/l, preferably of over 0.8 mol/l, are particularly preferred. Glycine and/or glutamine in an amount of more than 0.5 mol/l, preferably more than 0.8 mol/l, can also be additionally added to these mixtures. Moreover, the addition of soluble calcium salts, for example, in the form of calcium chloride, in concentrations of more than 0.5 mmol/l, preferably more than 1 mol/l, is advantageous.

The solution stabilized in this way is heated for 5 to 50 hours, preferably 8 to 20 hours, at 40 to 95° C., temperatures between 50 and 70° C., and in particular between 55 and 65° C., being preferred. The protein solutions stabilized according to the invention are also suitable for viral depletion by means of filtration, preferably nanofiltration, or by means of centrifugation or for treatment with bactericidal or virucidal agents or with detergents. The last-mentioned process is known as "solvent detergent treatment".

The invention is illustrated by the following example:

EXAMPLE

An aqueous protein solution which contained factor VIII in enriched form was mixed with sucrose up to a concentration of 1.75 g/ml. This solution was divided into a number of batches to which glycine or glutamate and arginine were admixed in order to achieve concentrations of 0.8 to 2 mol/l for each of the amino acids. The solutions stabilized in this way were heated in a water bath at 600 C. for 10 hours. Before and after heating, a sample of each of these batches was taken for analysis. The factor VIII activities were in each case investigated according to two known test methods, namely the "clotting test" and a chromogenic test (Coamatic@ FVIII). The protein activity was calculated for each batch and compared with the activity before pasteurization.

The first batch was stabilized according to the process disclosed in DE-A-29 16 711, while the second batch was stabilized according to the invention.

The results are shown in the following table:

| Batch | Yield (%) |
|---|---|
| 1. Sucrose: 1.75 g/ml<br>Glycine: 1.8 mol/l<br>$CaCl_2$ 0.05 mol/l | 82 |
| 2. Sucrose: 1.75 g/ml<br>Na glutamate: 1.5 mol/l<br>Arginine: 1.5 mol/l | 97 |

Thus, while the stabilization described in DE-A-29 16 711 using a sugar and an amino acid such as glycine caused a certain stabilization of factor VIII, Batch 2 clearly shows that the addition of arginine and sodium glutamate according to the invention achieved a considerably higher stabilization which left intact almost the total biological activity of the factor VIII employed.

We claim:

1. A stabilized protein preparation, which is protected against loss of activity during pasteurization by the addition of stabilizers wherein said preparation comprises stabilizers which comprise more than 1.5 g/ml of one or more saccharides as a mixture with more than 0.8 mol/l each of two or more amino acids chosen from arginine, lysine, histidine, phenylalanine, tryptophan, tyrosine, aspartic acid or a salt thereof, and glutamic acid or a salt thereof;

wherein one of said amino acids is glutamate; and wherein the stabilized protein preparation is an aqueous protein solution and contains no antithrombin III.

2. The stabilized protein preparation as claimed in claim 1, wherein the preparation further comprises glycine, glutamine, or glycine and glutamine together.

3. The stabilized protein preparation as claimed in claim 1, wherein the preparation further comprises a soluble calcium salt in an amount of at least 0.5 mmol/l.

4. A stabilized protein preparation as claimed in claim 1, comprising 1.75 g/ml sucrose, 1.5 mol/l sodium glutamate, and 1.5 mol/l arginine as stabilizers.

5. The stabilized protein preparation as claimed in claim 1, wherein the protein is one or more blood clotting factors chosen from FII, FV, FVII and FVIIa, FVIII, FIX, FX, FXII and their combination preparations, the von Willebrand factor (vWF), FVIII/vWF, or one or more proteins chosen from albumins, immunoglobulins, protease inhibitors, $\alpha$-2-antiplasmin, $\alpha$-1-antitrypsin, protein C, activated protein C, protein S, protein Z, tissue factor pathway inhibitor (TFPI), fibrinogen, fibronectin and plasminogen.

6. The stabilized protein preparation as claimed in claim 1, wherein the saccharide is a monosaccharide, a disaccharide or an oligosaccharide.

7. The stabilized protein preparation according to claim 1, wherein the preparation further comprises a soluble calcium salt in an amount of at least 1.0 mmol/l.

8. A process for the viral inactivation or viral depletion of the stabilized protein preparation according to claim 1, which comprises subjecting the stabilized protein preparation to a heat treatment at 40 to 95° C. for a period of 5 to 50 hours.

9. A process for the viral inactivation or viral depletion of the stabilized protein preparation according to claim 1, which comprises subjecting the stabilized protein preparation to viral depletion by means of filtration.

10. A process for the viral inactivation or viral depletion of the stabilized protein preparation according to claim 1, which comprises subjecting the stabilized protein preparation to a viral depletion by means of centrifugation.

11. A process for the viral inactivation or viral depletion of the stabilized protein preparation according to claim 1, which comprises subjecting the stabilized protein preparation to a treatment with detergents or bactericidal or virucidal agents.

* * * * *